United States Patent
Dash et al.

(10) Patent No.: US 8,674,129 B2
(45) Date of Patent: Mar. 18, 2014

(54) METHOD OF MAKING A DIORGANODIHALOSILANE

(75) Inventors: Aswini Dash, Midland, MI (US); Charles Hall, Crestwood, KY (US); Dimitris Katsoulis, Midland, MI (US); Robert Larsen, Midland, MI (US); Matthew McLaughlin, Midland, MI (US); Jonathan Wineland, Bedford, KY (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/880,160

(22) PCT Filed: Dec. 1, 2011

(86) PCT No.: PCT/US2011/062805
§ 371 (c)(1),
(2), (4) Date: Apr. 18, 2013

(87) PCT Pub. No.: WO2012/082385
PCT Pub. Date: Jun. 21, 2012

(65) Prior Publication Data
US 2013/0261279 A1    Oct. 3, 2013

Related U.S. Application Data

(60) Provisional application No. 61/424,120, filed on Dec. 17, 2010.

(51) Int. Cl.
*C07F 7/00* (2006.01)

(52) U.S. Cl.
USPC ........................................................ 556/466

(58) Field of Classification Search
USPC ..................... 556/443, 472, 474, 478, 466
See application file for complete search history.

(56) References Cited

U.S. PATENT DOCUMENTS

| | | | |
|---|---|---|---|
| 2,403,370 | A | 7/1946 | Hurd |
| 2,888,476 | A | 5/1959 | Little et al. |
| 3,057,686 | A | 10/1962 | Muetterties |
| 4,314,908 | A | 2/1982 | Downing et al. |
| 4,526,769 | A | 7/1985 | Ingle et al. |
| 4,836,997 | A | 6/1989 | Lepage et al. |
| 4,888,435 | A | 12/1989 | Chadwick et al. |
| 4,946,980 | A | 8/1990 | Halm et al. |
| 4,973,725 | A | 11/1990 | Lewis et al. |
| 6,156,380 | A | 12/2000 | Aramata et al. |
| 6,790,749 | B2 | 9/2004 | Takemura et al. |
| 6,887,448 | B2 | 5/2005 | Block |
| 7,212,778 | B2 | 5/2007 | Hisakuni |
| 7,223,879 | B2 | 5/2007 | Buchwald et al. |
| 7,442,824 | B2 | 10/2008 | Paetzold et al. |
| 7,716,590 | B1 | 5/2010 | Nathan |
| 7,728,176 | B2 | 6/2010 | Masaoka |
| 2005/0074387 | A1 | 4/2005 | Bulan et al. |
| 2007/0149798 | A1* | 6/2007 | Ogawa et al. ............... 556/466 |
| 2010/0280295 | A1 | 11/2010 | Armbruester |

FOREIGN PATENT DOCUMENTS

| | | |
|---|---|---|
| DE | 3024319 | 1/1982 |
| DE | 4041644 A1 | 6/1992 |
| DE | 19654154 | 6/1997 |
| JP | 51-23226 | 2/1976 |
| JP | 2009111202 | 5/2009 |
| WO | 2012-123159 | 9/2012 |

OTHER PUBLICATIONS

Dallas T. Hurd, The Vapor Phase Alkylation and Hydrogenation of Chlorosilanes, J. Am. Chem. Soc., 1945, 67 (9), pp. 1545-1548.

Eaborn, C. et al., Further studies on reactions of organic halides with disilanes catalysed by transition metal complexes, Journal of Organometallic Chemistry, vol. 225, 1982, pp. 331-341.

Golubtsov, S.A. et al., Role of the Products of Partial Chlorination of Silicon in the Formation of Methyltrichlorosilane, Russian Chemical Bulletin, vol. 21, No. 3 (1972), pp. 584-586.

H. Walter, Mechanism of the silicide-catalysed hydrodehalogenation of silicon tetrachloride to trichlorosilane, J. Chem. Soc., Faraday Trans., 1996,92, 4605-4608.

Juszczyk et al., of Pd/SiO2 catalysts during high temperature reduction., Department of Catalysis on Metals, Institute of Physical Chemistry, Polish Academy of Sciences, Warsaw, Pol. Catalysis Letters (2002), 78(1-4), 95-98.

Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.

Lobusevich, N.P. et al., Reactions During Direct Synthesis of Alkylchlorosilanes., vol. 48, No. 11, 1978, pp. 2534-2541.

Moreno-Manas, Marcial et al., Formation of Carbon-Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.

Beccalli, Egle M., et al., C—C, C—O, C—N Bond Formation on sp2 Carbon by Palladium(II)-Catalyzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.

Methivier, et al., Pd/SiC catalysts. Characterization and catalytic activity for the methane total oxidation.. Institut de Recherches sur la Catalyse-CNRS, conventionne a l'Universite Claude Bernard Lyon 1, Villeurbanne, Fr. Journal of Catalysis (1998), 173(2), 374-382.

(Continued)

*Primary Examiner* — Fereydoun G Sajjadi
*Assistant Examiner* — Kofi Adzamli
(74) *Attorney, Agent, or Firm* — Matthew T. Fewkes

(57) ABSTRACT

A method of making a diorganodihalosilane contacting an organotrihalosilane according to the formula $RSiX_3$ (I) with hydrogen in the presence of a metal catalyst comprising at least two metals and at a temperature from 300 to 800° C. to form a diorganodihalosilane, wherein R is $C_1$-$C_{10}$ Q hydrocarbyl, X is halo, and two of the at least two metals are chosen from at least one of (i) copper and palladium, (ii) copper and gold, (iii) indium and iridium or (iv) iridium and rhenium.

18 Claims, No Drawings

(56) References Cited

OTHER PUBLICATIONS

Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12), 1841-1848.

Tanaka, Miyoko et al., Nanomaterials Laboratory, National Institute for Materials Science, Tsukuba, Sakura, Japan. Journal of Crystal Growth (2002), 237-239(Pt. 1), 254-258.

Terao, Jun et al., Transition metal-catalyzed C—C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro-Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon-carbon coupling reactions catalyzed by heterogeneous palladium catalysts., Institute fuer Chemie, Humboldt-Universitaet Berlin, Berlin, Germany. Chemical Reviews (Washington, DC, United States) (2007), 107(1), 133-173.

\* cited by examiner

METHOD OF MAKING A DIORGANODIHALOSILANE

CROSS REFERENCE TO RELATED APPLICATIONS

This application is a U.S. national stage filing under 35 U.S.C. §371 of PCT Application No. PCT/US11/062805 filed on 1 Dec. 2011, currently pending, which claims the benefit of U.S. Provisional Patent Application No. 61/424,120 filed 17 Dec. 2010 under 35 U.S.C. §119 (e). PCT Application No. PCT/US11/062805 and U.S. Provisional Patent Application No. 61/424,120 are hereby incorporated by reference.

FIELD OF THE INVENTION

The present invention relates to a method of making a diorganodihalosilane comprising contacting an organotrihalosilane with hydrogen in the presence of a metal catalyst.

BACKGROUND OF THE INVENTION

Diorganodihalosilanes are hydrolyzed to produce a wide range of polyorganosiloxanes, which are sold into many different industries. Typically, diorganodihalosilanes are produced commercially by the Mueller-Rochow Direct Process, which comprises passing an organohalide, such as methyl chloride, over zero-valent silicon in the presence of a copper catalyst and various promoters. The Direct Process produces a mixture of organohalosilanes, the most valuable of which is dimethyldichlorosilane.

The Direct Process uses zero-valent silicon. A typical commercial process to make zero-valent silicon comprises the carbothermic reduction of $SiO_2$ in an electric arc furnace at extremely high temperatures. Generation of these extreme temperatures requires significant amounts of energy, which adds significant cost to the process of producing zero-valent silicon. Consequently, the use of zero-valent silicon also adds significant costs to the production of diorganodihalosilanes by the Direct Process.

In addition to the Direct Process, diorganodihalosilanes have been produced by the alkylation of silicon tetrachloride and various methylchlorosilanes by passing the vapors of these chlorosilanes together with an alkyl halide over finely divided aluminum or zinc at elevated temperatures. However, this process results in the production of a large amount of aluminum chloride or zinc chloride, which is costly to dispose of on a commercial scale.

Therefore, there is a need for a more economical method of producing diorganodihalosilanes that avoids the need for the direct use of zero-valent silicon and that does not require the costly disposal of large amounts of byproducts.

BRIEF SUMMARY OF THE INVENTION

The present invention is directed to a method of making a diorganodihalosilane comprising contacting an organotrihalosilane according to the formula $RSiX_3$ (I) with hydrogen in the presence of a metal catalyst comprising at least two metals and at a temperature from 300 to 800° C. to form a diorganodihalosilane, wherein R is $C_1$-$C_{10}$ hydrocarbyl, X is halo, and two of the at least two metals are chosen from at least one of (i) copper and palladium, (ii) copper and gold, (iii) indium and iridium or (iv) iridium and rhenium.

Since the method of the invention does not directly employ zero-valent silicon, the method may be more economical and require less energy than other methods in the art for producing a diorganodihalosilane. The method also does not have disposal issues related to producing large quantities of aluminum or zinc chloride.

The diorganodihalosilanes produced according to the method of the present invention may be hydrolyzed in known processes to produce polysiloxanes, which find use in many industries and applications.

DETAILED DESCRIPTION OF THE INVENTION

A method of making a diorganodihalosilane, the method comprising:

contacting an organotrihalosilane according to the formula $RSiX_3$ (I) with hydrogen in the presence of a metal catalyst comprising at least two metals and at a temperature from 300 to 800° C. to form a diorganodihalosilane, wherein R is $C_1$-$C_{10}$ hydrocarbyl, X is halo, and two of the at least two metals are chosen from at least one of (i) copper and palladium, (ii) copper and gold, (iii) indium and iridium or (iv) iridium and rhenium.

The organotrihalosilane is according to the formula $RSiX_3$ (I), wherein R is $C_1$-$C_{10}$ hydrocarbyl, and X is halo, for example, chloro, bromo, fluoro, or iodo.

The hydrocarbyl groups represented by R typically have from 1 to 10 carbon atoms, alternatively from 1 to 6 carbon atoms, alternatively from 1 to 4 carbon atoms, alternatively 1 carbon atom. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, cyclohexyl, and methylcyclohexyl; aryl, such as phenyl and napthyl; alkaryl, such as tolyl and xylyl; aralkyl, such as benzyl and phenethyl; alkenyl, such as vinyl, allyl, and propenyl; aralkenyl, such as styryl and cinnamyl; and alkynyl, such as ethynyl and proynyl.

Examples of the organotrihalosilane include methyltrichlorosilane, methyltribromosilane, methyltrifluorosilane, methyltriiodosilane, ethyltrichlorosilane, ethyltribromosilane, ethyltrifluorosilane, ethyltriiodosilane, propyltrichlorosilane, propyltribromosilane, propyltrifluorosilane, propyltriiodosilane, butyltrichlorosilane, butyltribromosilane, butyltrifluorosilane, butyltriiodosilane, phenyltrichlorosilane, phenyltribromosilane, phenyltrifluorosilane, phenyltriiodosilane. benzyltrichlorosilane, benzyltribromosilane, benzyltrifluorosilane, and benzyltriiodosilane. In one embodiment, the organotrihalosilane is methyltrichlorosilane.

Methods of making organotrihalosilanes are known in the art. Many of these compounds are available commercially.

The metal catalyst comprises at least two metals, and two of the at least two metals are chosen from at least one of (i) copper and palladium, (ii) copper and gold, (iii) indium and iridium or (iv) iridium and rhenium. In one embodiment, the at least two metals are copper and palladium.

The oxidation number of the metals is typically from 0 to 4, alternatively 0 to 2, alternatively 0; the oxidation number of the copper is typically from 0 to 2, alternatively 0; the oxidation number of gold is typically from 0 to 3, alternatively 0; the oxidation number of indium is typically from 0 to 3, alternatively 0; the oxidation number of iridium is typically from 0 to 4, alternatively 0; and the oxidation number of rhenium is typically from 0 to 4, alternatively 0.

The metal catalyst also typically comprises a support. Examples of supports include, but are not limited to, oxides of aluminum, titanium, zirconium, and silicon; and carbon, such as activated carbon, carbon nanotubes, fullerenes, graphene and other allotropic forms of carbon. In one embodiment, the support is activated carbon. The metals of the metal catalyst may be on the same support, or they may be on separate supports mixed together.

When the metal catalyst comprises a support, the metal catalyst typically comprises, based on the combined weight of the metals and support, from 0.1 to less than 100% (w/w), alternatively from 0.1 to 50% (w/w), alternatively from 0.1 to 35% (w/w), of the metals combined.

The weight ratio of the two metals of the metal catalyst chosen from at least one of (i) copper and palladium, (ii) copper and gold, (iii) indium and iridium or (iv) iridium and rhenium to each other is typically from 10,000 to 0.0001, alternatively from 1000 to 0.001, alternatively from 100 to 0.01.

The metal catalyst can have a variety of physical forms including, but not limited to, lumps, granules, flakes, and powder.

Examples of the metal catalyst include, but are not limited to, zero-valent palladium and zero-valent copper on an activated carbon support at the following weight percentages: 0.5% (w/w) palladium, 33% (w/w) copper, and 66.5% (w/w) activated carbon; 15% (w/w) palladium, 15% (w/w) copper, and 70% (w/w) activated carbon; 33% (w/w) palladium, 0.5% (w/w) copper, and 66.5% (w/w) activated carbon; and 7.7% (w/w) palladium, 5.8% (w/w) copper, and 86.5% (w/w) activated carbon; zero-valent copper and zero-valent gold at the following weight percentages: 0.5% (w/w) copper, 33% (w/w) gold, and 66.5% (w/w) activated carbon; 15% (w/w) copper, 15% (w/w) gold, and 70% (w/w) activated carbon; 33% (w/w) copper, 0.5% (w/w) gold, and 66.5% (w/w) activated carbon; and 7.7% (w/w) copper, 5.8% (w/w) gold, and 86.5% (w/w) activated carbon; zero-valent indium and zero-valent iridium at the following percentages: 0.5% (w/w) indium, 33% (w/w) iridium, and 66.5% (w/w) activated carbon; 15% (w/w) indium, 15% (w/w) iridium, and 70% (w/w) activated carbon; 33% (w/w) indium, 0.5% (w/w) iridium, and 66.5% (w/w) activated carbon; and 7.7% (w/w) indium, 5.8% (w/w) iridium, and 86.5% (w/w) activated carbon; and zero-valent rhenium and zero-valent iridium at the following percentages: 0.5% (w/w) rhenium, 33% (w/w) iridium, and 66.5% (w/w) activated carbon; 15% (w/w) rhenium, 15% (w/w) iridium, and 70% (w/w) activated carbon; 33% (w/w) rhenium, 0.5% (w/w) iridium, and 66.5% (w/w) activated carbon; and 7.7% (w/w) rhenium, 5.8% (w/w) iridium, and 86.5% (w/w) activated carbon.

The metal catalyst may be prepared on a support by dissolving metal salts, such as palladium chloride and cuprous chloride, in a solvent, such as water or acid, applying this solution to the support, such as activated carbon, and reducing the salts on the surface of the support. For example, palladium (II) chloride and copper(II) chloride can be dissolved in hydrochloric acid and mixed with activated carbon. Excess solution can then be removed, and the activated carbon, $PdCl_2$, and $CuCl_2$ mixture dried. The $PdCl_2$ and $CuCl_2$ can then be reduced on the activated carbon with hydrogen at elevated temperatures, typically about 500° C., to give the metal catalyst. One skilled in the art would understand that the order of addition and reduction and multistep addition of salts and subsequent reduction can also be carried out to prepare the metal catalyst. For example, it is contemplated that the metal catalyst may be prepared by reducing a palladium salt on a support and reducing a copper salt on a separate support followed by mixing the two supports. A method of making the supported catalyst is also described in detail in the examples section below.

The reactor for the method of the invention can be any reactor suitable for the combining of gases and solids. For example, the reactor configuration can be a packed bed, stirred bed, vibrating bed, moving bed, a fluidized bed, or reactor tube. To facilitate reaction, the reactor should have means to control the temperature of the reaction zone.

The temperature at which the hydrogen and the organotrihalosilane are contacted in the presence of the metal catalyst is typically from 300 to 800° C.; alternatively from 400 to 700° C.; alternatively from 500 to 700° C.

The pressure at which the hydrogen and the organotrihalosilane are contacted in the presence of the metal catalyst can be sub-atmospheric, atmospheric, or super-atmospheric. For example, the pressure is typically from 0 to 1000 kilopascals gauge (kPag); alternatively from alternatively from 0 to 500 kPag; alternatively from 0 to 120 kPag. As used herein, 0 kPag is intended to mean atmospheric pressure.

The mole ratio of hydrogen to organotrihalosilane is typically from 1 to 2300, alternatively from 3 to 2000, alternatively from 3 to 1000, alternatively from 3 to 400.

The residence time for the hydrogen and organotrihalosilane is sufficient to form the diorganodihalosilane. For example, a sufficient residence time for the hydrogen and organotrihalosilane is typically at least 0.01 seconds (s); alternatively at least 0.1 s; alternatively from 0.1 s to 10 min; alternatively from 0.1 s to 1 min; alternatively from 1 s to 10 s. As used herein, "residence time" means the time for one reactor volume of reactant gases (i.e., hydrogen and organotrihalosilane) to pass through a reactor charged with the metal catalyst. The desired residence time may be achieved by adjusting the flow rate of the hydrogen and organotrihalosilane.

The hydrogen and organotrihalosilane are typically fed to the reactor simultaneously; however, other methods of combining, such as by separate pulses, are also envisioned.

The metal catalyst is in a catalytic effective amount. As used herein, a "catalytic effective amount" is a sufficient amount of metal catalyst to form the diorganodihalosilane, described below, when the hydrogen and organotrihalosilane are contacted in the presence of the metal catalyst. For example, a catalytic effective amount of metal catalyst is typically at least 0.01 mg catalyst/$cm^3$ of reactor volume; alternatively at least 0.5 mg catalyst/$cm^3$ of reactor volume; alternatively from 1 to 10,000 mg catalyst/$cm^3$ of reactor volume.

The method of the invention may be conducted continuously or semi-continuously. As used herein, "continuously" means that the metal catalyst, organotrihalosilane and hydrogen are added as needed to the reactor to continue the reaction, and the product, unreacted starting materials, and byproducts are removed as they are produced. As used herein, "semi-continuously" means that the organotrihalosilane and the hydrogen are fed to the reactor containing the metal catalyst while the diorganodihalosilane product, organotrihalosilane, hydrogen, and any byproducts are removed until a point when the process is stopped and then later restated.

The method of the invention is typically conducted on a semi-continuous basis. The method is typically conducted until the diorganodihalosilane production rate falls below predetermined limits, at which time the metal catalyst may be replaced or regenerated. For example, the method is typically conducted until the diorganodihalosilane production rate falls below 95%, alternatively below 85%, alternatively from 10 to 85%, of an initial diorganodihalosilane production rate for the same run. The "initial diorganodihalosilane production rate" is a diorganodihalosilane production rate from an earlier time in the same run and may be different than the first diorganodihalosilane production rate from a particular run. For example, the initial diorganodihalosilane production rate may be the rate when the process first reaches a steady state.

The method of the invention may also comprise regenerating the metal catalyst after the metal catalyst has been contacted with the organotrihalosilane and hydrogen. The metal catalyst may be regenerated by contacting the metal catalyst with a hydrochlorination or chlorination agent, such as, but not limited to, HCl or $Cl_2$. The metal catalyst is typically contacted with the hydrochlorination agent at a temperature from 100 to 800° C., alternatively from 200 to 600° C., alternatively from 250 to 550° C., and from atmospheric to super-atmospheric pressure, alternatively from 0 to 2000 kPag, alternatively from 5 to 500 kPag. The regeneration of the metal catalyst may be conducted in a reactor as described and exemplified above. The regeneration of the metal catalyst is typically conducted until little or no silicon species are produced from the contacting of the hydrochlorination agent with the metal catalyst. The regenerated metal catalyst typically may then be used in the process of the invention again.

The method of the invention may also comprise purging the reactor prior to the contacting of the hydrogen and organotrihalosilane. As used herein, "purging" means to introduce a gas stream to the reactor containing the metal catalyst to remove unwanted materials. Unwanted materials are, for example, $O_2$ and $H_2O$. Purging may be accomplished with an inert gas, such as argon, nitrogen, or helium or with a reactive gas, such as silicon tetrachloride, which reacts with moisture thereby removing it.

The method of the invention may also comprise activating the metal catalyst prior to the contacting of the hydrogen and the organotrihalosilane in the presence of the metal catalyst. Activation of the metal catalyst is accomplished by treating the metal catalyst with hydrogen at elevated temperature, typically around 500° C., for a period of time, typically 1 to 3 hours.

The method may further comprise pre-heating and gasifying the organotrihalosilane by known methods prior to contacting with the hydrogen in the presence of the metal catalyst. Alternatively, the process may further comprise bubbling the hydrogen through the organotrihalosilane to vaporize the organotrihalosilane prior to the contacting in the presence of the catalyst.

The method of the invention may also comprise conducting the contacting is conducted in the absence of a polysilanes. A polysilanes is compound having an Si—Si bond.

The process may further comprise recovering the diorganodihalosilane. The diorganodihalosilane may be recovered by, for example, removing gaseous diorganodihalosilane and any other gases from the reactor followed by isolation of the diorganodihalosilane by distillation.

The method of the invention produces a diorganodihalosilane having the formula $R_2SiX_2$, wherein R and X are as defined and exemplified above for the organotrihalosilane. Examples of diorganodihalosilanes prepared according to the present process include, but are not limited to, $(CH_3)_2SiCl_2$, $(CH_3)_2SiBr_2$, $(CH_3)_2SiI_2$, $(CH_3CH_2)_2SiCl_2$, $(CH_3CH_2)_2SiBr_2$, $(CH_3CH_2)_2SiI_2$, $(CH_3CH_2CH_2)_2SiCl_2$, $(CH_3CH_2CH_2)_2SiBr_2$, $(CH_3CH_2CH_2)_2SiI_2$, $(CH_3)(Ph)SiCl_2$, $(CH_3)(Ph)SiBr_2$, $(CH_3)(Ph)SiI_2$, $(CH_3CH_2)(Ph)SiCl_2$, $(CH_3CH_2)(Ph)SiBr_2$, $(CH_3CH_2)(Ph)SiI_2$, $(CH_3CH_2CH_2)(Ph)SiCl_2$, $(CH_3CH_2CH_2)(Ph)SiBr_2$, and $(CH_3CH_2CH_2)(Ph)SiI_2$, where Ph means phenyl.

The method of the present invention produces a diorganodihalosilane from hydrogen and an organotrihalosilane. Since the method does not use zero-valent silicon directly, the method may produce diorganodihalosilane using less energy and more economically than methods that use zero-valent silicon directly. Further, the process of the invention does not produce large amounts of metal byproducts requiring disposal.

The process of the present invention produces a diorganodihalosilane that can be hydrolyzed in known processes for producing polysiloxanes. Polysiloxanes find use in many industries and applications.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 2

List of abbreviations used in the examples.

| Abbreviation | Word |
|---|---|
| g | gram |
| Me | methyl |
| wt | weight |
| % | percent |
| mol | mole |
| min | minutes |
| ° C. | degrees Celsius |
| mL | milliliters |
| sccm | standard cubic centimeters per minute |
| Yield (%) | mole %, based on all silicon-containing compounds, of diorganodihalosilane exiting the reactor |
| GC | gas chromatography |
| Temp. | temperature |
| TCD | thermal conductivity detector |
| FID | Flame Ionization Detector |
| P | pressure |
| psi | pounds/$in^2$ |
| μL | microliter |

Method of Producing Catalyst

A metal chloride was dissolved in water or hydrochloric acid. This solution was mixed with activated carbon and subjected to a vacuum for 20-30 minutes. The excess liquid was decanted, and the remaining activated carbon and metal salt was dried in an oven at 120-150° C.

About 0.5 g of the oven-dried activated carbon and metal salt were loaded into an open-ended glass tube, which was loaded into a Lindberg/Blue Minimite 1 inch tube furnace, and contacted with 30-40 sccm $H_2$ at 500° C. for 2 hours or 5-10 sccm $H_2$ at 450° C. for about 15 hours. The $H_2$ was ultra high purity from Airgas. The flow of hydrogen was controlled with an MKS 1179A mass flow controller.

Reaction Apparatus

The reaction apparatus consisted of an open-ended glass tube with quartz wool to hold the metal catalyst in place. The tube was connected to a flow reactor comprising a Lindberg/Blue Minimite 1 inch tube furnace and an MKS 1179A mass flow controller to control gas flow. In elevated pressure runs, the glass tube was inserted into a steel tube with an inner diameter just big enough to fit the glass tube. An O-ring was fitted over the glass tube at the inlet to prevent flow of gases around the outside. A back-pressure regulator (0-500 psi) from GO Regulators was attached to the reactor at the outlet of the tube furnace.

Reagents

The hydrogen was ultra high purity hydrogen from Airgas (Radnor, Pa.). The activated carbon and metal salts were purchased from Sigma Aldrich (Milwaukee, Wis.). The methyltrichlorosilane was 99% from Sigma Aldrich (Milwaukee, Wis.).

Product Analysis

The effluent of the reactor containing the products and byproducts was passed through an actuated 6-way valve (Vici) with constant 100 μL injection loop before being discarded. Samples were taken from the reaction stream by actuating the injection valve and the 100 μL sample passed directly into the injection port of a 6890A Agilent GC equipped with a TCD and a FID for analysis.

Flow Rates

Methyltrichlorosilane flow rate ratios were determined using known thermodynamic principles governing the operation of a bubbler containing a vaporizable liquid and the flow rate of hydrogen at standard temperature and pressure.

Example 1

In a flow reactor, about 0.5 g of catalyst, comprising 7.7% (w/w) Pd and 5.8% (w/w) Cu on activated carbon, were loaded into a glass tube. Activation of the metal catalyst was performed with 10 sccm $H_2$ at 450° C. for about 15 hours. The temperature of the reactor was decreased to about 400° C. and the reaction was started by passing $H_2$ through the $MeSiCl_3$ bubbler. Samples were taken from the reaction stream and injected into a GC for analysis using an online switching valve. The reaction was run while varying the following conditions: flow rate of hydrogen, and $MeSiCl_3$ bubbler temperature. The metal catalyst activation and reaction were done without applying back pressure to the system. $(CH_3)_2SiCl_2$ was produced at the conditions and yields listed in Table 2.

TABLE 2

$(CH_3)_2SiCl_2$ production with Pd and Cu on activated carbon.

| Temp. (° C.) | Time (min) | $H_2$ (sccm) | $CH_3SiCl_3$ (sccm) | Bubbler Temp (° C.) | $(CH_3)_2SiCl_2$ Yield (%) |
|---|---|---|---|---|---|
| 500 | 296 | 20 | 2.9 | 28.0 | 11.8 |
| 500 | 336 | 5 | 1.1 | 27.9 | 14.7 |
| 500 | 372 | 10 | 1.0 | 14.6 | 14.7 |
| 500 | 407 | 10 | 0.5 | 0.6 | 14.3 |
| 500 | 459 | 10 | 0.3 | −12.8 | 13.1 |

Example 2

In a flow reactor, about 0.5 g of catalyst, comprising 17% (w/w) Pd and 1.2% (w/w) Cu on activated carbon, were loaded into a glass tube. Activation of the metal catalyst was performed with 75 sccm $H_2$ at 500° C. for about 2.5 hours. The temperature of the reactor was decreased to about 300° C. and the reaction was started by passing $H_2$ through the $MeSiCl_3$ bubbler. Samples were taken from the reaction stream and injected into a GC for analysis using an online switching valve. The reaction was run while varying the following conditions: reaction temperature, flow rate of hydrogen, and $MeSiCl_3$ bubbler temperature. The metal catalyst activation and reaction were done without applying back pressure to the system. $(CH_3)_2SiCl_2$ was produced at the conditions and yield listed in Table 3.

TABLE 3

$(CH_3)_2SiCl_2$ production with Pd and Cu on activated carbon.

| Temp. (° C.) | Time (min) | $H_2$ (sccm) | $CH_3SiCl_3$ (sccm) | Bubbler Temp (° C.) | $(CH_3)_2SiCl_2$ Yield (%) |
|---|---|---|---|---|---|
| 300 | 15 | 10 | 1.9 | 26.9 | 0.2 |
| 400 | 53 | 10 | 1.9 | 27.2 | 9.4 |
| 450 | 88 | 10 | 2.0 | 27.5 | 14.6 |
| 500 | 125 | 10 | 1.9 | 27.4 | 13.5 |
| 500 | 160 | 2 | 0.5 | 27.8 | 13.6 |
| 500 | 195 | 20 | 3.1 | 27.9 | 8.1 |
| 450 | 238 | 10 | 1.1 | 14.6 | 7.7 |
| 450 | 274 | 10 | 0.5 | −1.1 | 10.8 |
| 450 | 349 | 10 | 0.2 | −14.8 | 12.7 |

Example 3

In a flow reactor, about 0.8 g of catalyst, comprising 20.1% (w/w) Au and 1.9% (w/w) Cu on activated carbon, were loaded into a glass tube. Activation of the metal catalyst was performed with 10 sccm $H_2$ at 450° C. for about 15 hours. The temperature of the reactor was decreased to about 300° C. and the reaction was started by passing $H_2$ through the $MeSiCl_3$ bubbler. Samples were taken from the reaction stream and injected into a GC for analysis using an online switching valve. The reaction was run while varying the following conditions: reaction temperature, flow rate of hydrogen, and $MeSiCl_3$ bubbler temperature. The metal catalyst activation and reaction were done without applying back pressure to the system. $(CH_3)_2SiCl_2$ was produced at the conditions and yield listed in Table 4.

TABLE 4

$(CH_3)_2SiCl_2$ production with Au and Cu on activated carbon.

| Temp. (° C.) | $H_2$ (sccm) | $CH_3SiCl_3$ (sccm) | Bubbler Temp (° C.) | $(CH_3)_2SiCl_2$ Yield (%) |
|---|---|---|---|---|
| 300 | 10 | 1.9 | 25.5 | 0.2 |
| 400 | 10 | 1.9 | 26.2 | 0.6 |
| 500 | 10 | 1.9 | 27.0 | 6.3 |

Example 4

In a flow reactor, about 0.5 g of catalyst, comprising 5.6% (w/w) Ir and 0.5% (w/w) In on activated carbon, were loaded into a glass tube. Activation of the metal catalyst was performed with 100 sccm $H_2$ at 500° C. for about 2 hours. The reaction was started by passing $H_2$ through the $MeSiCl_3$ bubbler. Samples were taken from the reaction stream and injected into a GC for analysis using an online switching valve. The reaction was run while varying the following conditions: reaction temperature, flow rate of hydrogen, and $MeSiCl_3$ bubbler temperature. The metal catalyst activation and reaction were done without applying back pressure to the system. $(CH_3)_2SiCl_2$ was produced at the conditions and yield listed in Table 5.

TABLE 5

(CH$_3$)$_2$SiCl$_2$ production with Ir and In on activated carbon.

| Temp. (° C.) | H$_2$ (sccm) | CH$_3$SiCl$_3$ (sccm) | Bubbler Temp (° C.) | (CH$_3$)$_2$SiCl$_2$ Yield (%) |
|---|---|---|---|---|
| 500 | 100 | 26.5 | 23 | 0.9 |
| 500 | 3 | 0.8 | 23 | 2.7 |
| 400 | 3 | 0.8 | 23 | 1.0 |
| 300 | 3 | 0.8 | 23 | 0.2 |
| 600 | 3 | 0.8 | 23 | 6.1 |
| 600 | 3 | 0.1 | −15 | 3.2 |
| 600 | 3 | 0.3 | 1 | 3.8 |
| 500 | 3 | 0.1 | −15 | 1.8 |

Example 5

In a flow reactor, about 0.5 g of catalyst, comprising 2.2% (w/w) Ir and 1.9% (w/w) Re on activated carbon, were loaded into a glass tube. Activation of the metal catalyst was performed with 100 sccm H$_2$ at 500° C. for about 2 hours. The reaction was started by passing H$_2$ through the MeSiCl$_3$ bubbler. Samples were taken from the reaction stream and injected into a GC for analysis using an online switching valve. The reaction was run while varying the following conditions: reaction temperature, flow rate of hydrogen, and MeSiCl$_3$ bubbler temperature. The metal catalyst activation and reaction were done without applying back pressure to the system. (CH$_3$)$_2$SiCl$_2$ was produced at the conditions and yield listed in Table 6.

TABLE 6

(CH$_3$)$_2$SiCl$_2$ production with Ir and Re on activated carbon.

| Temp. (° C.) | H$_2$ (sccm) | CH$_3$SiCl$_3$ (sccm) | Bubbler Temp (° C.) | (CH$_3$)$_2$SiCl$_2$ Yield (%) |
|---|---|---|---|---|
| 500 | 100 | 26.5 | 23 | 2.2 |
| 500 | 3 | 0.8 | 23 | 4.8 |
| 600 | 3 | 0.8 | 23 | 7.2 |
| 600 | 3 | 0.08 | −20 | 9.7 |
| 500 | 3 | 0.7 | 20 | 4.6 |
| 500 | 3 | 0.1 | −15 | 4.0 |

Comparative Example 1

In a flow reactor, about 1.0 g of catalyst, comprising 17.1% (w/w) Cu on activated carbon, were loaded into a glass tube. Activation of the metal catalyst was performed with 6 sccm H$_2$ at 400° C. for about 15 hours, then 40 sccm H$_2$ for 2 hours. The temperature of the reactor was decreased to about 200° C. and the reaction was started by passing H$_2$ through the MeSiCl$_3$ bubbler. The reaction was run at 500° C. and with a MeSiCl$_3$ bubbler temperature of 24.9° C. and at 6 sccm H$_2$. The metal catalyst activation and reaction were done without applying back pressure to the system. Three samples were taken from the reaction stream and injected into a GC for analysis using an online switching valve at different times. (CH$_3$)$_2$SiCl$_2$ was produced at percent yield below 1%.

Comparative Example 2

In a flow reactor, about 0.8 g of catalyst, comprising 16.9% (w/w) Au on activated carbon, were loaded into a glass tube. Activation of the metal catalyst was performed with 6 sccm H$_2$ at 450° C. for about 15 hours. The temperature of the reactor was decreased to about 300° C. and the reaction was started by passing H$_2$ through the MeSiCl$_3$ bubbler. The reaction was run at 300° C., a flow rate of 6 sccm hydrogen, and a MeSiCl$_3$ bubbler temperature of 26.7° C. The metal catalyst activation and reaction were done without applying back pressure to the system. A samples was taken from the reaction stream and injected into a GC for analysis using an online switching valve, and (CH$_3$)$_2$SiCl$_2$ was produced at 0.2% yield.

Comparative Example 3

In a flow reactor, about 0.6 g of catalyst, comprising 18.8% (w/w) Ir on activated carbon, were loaded into a glass tube. Activation of the metal catalyst was performed with 10 sccm H$_2$ at 450° C. for about 15 hours. The temperature of the reactor was decreased to about 300° C. and the reaction was started by passing H$_2$ through the MeSiCl$_3$ bubbler. Samples were taken from the reaction stream and injected into a GC for analysis using an online switching valve. The reaction was run while varying the reaction temperature from 400 to 700° C., flow rate of hydrogen from 5 to 10 sccm, and MeSiCl$_3$ bubbler temperature from −13 to 28° C. The metal catalyst activation and reaction were done without applying back pressure to the system. (CH$_3$)$_2$SiCl$_2$ was produced at yields below 1.6%.

Comparative Example 4

In a flow reactor, about 0.5 g of catalyst, comprising 22.6% (w/w) In on activated carbon, were loaded into a glass tube. Activation of the metal catalyst was performed with 100 sccm H$_2$ at 500° C. for about 2 hours. The reaction was started by passing H$_2$ through the MeSiCl$_3$ bubbler. The reaction was run at reaction temperature of 600° C., a 1000 sccm flow rate of hydrogen, and a MeSiCl$_3$ bubbler temperature of 23° C. The metal catalyst activation and reaction were done without applying back pressure to the system. A samples was taken from the reaction stream and injected into a GC for analysis using an online switching valve. (CH$_3$)$_2$SiCl$_2$ was produced at a yield of 0.2%.

Comparative Example 5

In a flow reactor, about 0.6 g of catalyst, comprising 5.9% (w/w) Re on activated carbon, were loaded into a glass tube. Activation of the metal catalyst was performed with 10 sccm H$_2$ at 450° C. for about 15 hours. The temperature of the reactor was decreased to 200° C., and the reaction was started by passing H$_2$ through the MeSiCl$_3$ bubbler. The reaction was run varying the reaction temperature from 300 to 500° C., at a 10 sccm flow rate of hydrogen, and varying the MeSiCl$_3$ bubbler temperature from −15 to 28° C. The metal catalyst activation and reaction were done without applying back pressure to the system. Samples was taken from the reaction stream and injected into a GC for analysis using an online switching valve. (CH$_3$)$_2$SiCl$_2$ was produced at a maximum yield of 1.7%.

Comparative Example 6

In a flow reactor, about 0.5 g of catalyst, comprising 9.2% (w/w) Pd and 1.1% (w/w) Rh on activated carbon, were loaded into a glass tube. Activation of the metal catalyst was performed with 5 sccm H$_2$ at 450° C. for about 15 hours. The temperature of the reactor was decreased to about 300° C. and the reaction was started by passing H$_2$ through the MeSiCl$_3$ bubbler. Samples were taken from the reaction stream and injected into a GC for analysis using an online switching valve. The reaction was run while varying the following conditions: reaction temperature, flow rate of hydrogen, and MeSiCl$_3$ bubbler temperature. The metal catalyst activation and reaction were done without applying back pressure to the system. (CH$_3$)$_2$SiCl$_2$ was produced at various temperature conditions and yields.

TABLE 6

(CH$_3$)$_2$SiCl$_2$ production with Pd and Rh on activated carbon.

| Temp. (° C.) | Time (min) | H$_2$ (sccm) | CH$_3$SiCl$_3$ (sccm) | Bubbler Temp (° C.) | (CH$_3$)$_2$SiCl$_2$ Yield (%) |
|---|---|---|---|---|---|
| 300 | 42 | 10 | 2.4 | 22.8 | 2.2 |
| 400 | 78 | 10 | 2.4 | 22.8 | 9.1 |
| 450 | 112 | 10 | 2.4 | 23.0 | 6.9 |
| 500 | 154 | 10 | 2.5 | 23.2 | 1.1 |
| 600 | 191 | 10 | 2.5 | 23.3 | 1.3 |
| 700 | 224 | 10 | 2.5 | 23.6 | 1.5 |
| 700 | 273 | 10 | 1.0 | 6.2 | 0.9 |

That which is claimed is:

1. A method of making a diorganodihalosilane, the method comprising:
   contacting an organotrihalosilane according to the formula RSiX$_3$ (I) with hydrogen in the presence of a metal catalyst comprising at least two metals and at a temperature from 300 to 800° C. to form a diorganodihalosilane, wherein R is C$_1$-C$_{10}$ hydrocarbyl, X is halo, and two of the at least two metals are chosen from at least one of (i) copper and palladium, (ii) copper and gold, (iii) indium and iridium or (iv) iridium and rhenium.

2. The method of claim 1, wherein the diorganodihalosilane is according to the formula R$_2$SiX$_2$.

3. The method of claim 1, further comprising recovering the diorganodihalosilane.

4. The method of claim 1, wherein R is methyl and X is chloro.

5. The method of claim 1, wherein the contacting is at a pressure of from 0 to 120 kPag.

6. The method of claim 1, wherein the temperature is from 400 to 700° C.

7. The method of claim 1, wherein the metal catalyst further comprises a support.

8. The method of claim 7, wherein the metal catalyst comprises from 0.1 to 35% (w/w) of the metal.

9. The method of claim 8, wherein the support is carbon.

10. The method of claim 1, wherein the mole ratio of the hydrogen to the organotrihalosilane is from 3 to 400.

11. The method of claim 1, wherein the organotrihalosilane and hydrogen have a contact time of 0.01 s to 10 min.

12. The method of claim 1, further comprising regenerating the metal catalyst after contacting with the organotrihalosilane and hydrogen.

13. The method of claim 1, further comprising activating the metal catalyst prior to the contacting of the hydrogen and the organotrihalosilane in the presence of the metal catalyst by treating the metal catalyst with hydrogen.

14. The method of claim 1, wherein the two of the at least two metals are copper and palladium.

15. The method of claim 1, wherein the two of the at least two metals are copper and gold.

16. The method of claim 1, wherein the two of the at least two metals are indium and iridium.

17. The method of claim 1, wherein the two of the at least two metals are iridium and rhenium.

18. A method of making a polyorganosiloxane, the method comprising:
   (1) contacting an organotrihalosilane according to the formula RSiX$_3$ (I) with hydrogen in the presence of a metal catalyst comprising at least two metals and at a temperature from 300 to 800° C. to form a diorganodihalosilane, wherein R is C$_1$-C$_{10}$ hydrocarbyl, X is halo, and two of the at least two metals are chosen from at least one of (i) copper and palladium, (ii) copper and gold, (iii) indium and iridium or (iv) iridium and rhenium; and
   (2) hydrolyzing the diorganodihalosilane.

\* \* \* \* \*